US009265189B2

(12) United States Patent
Sakamoto et al.

(10) Patent No.: US 9,265,189 B2
(45) Date of Patent: Feb. 23, 2016

(54) METHOD FOR REDUCING DAMAGE BY HARMFUL ORGANISMS IN CORN CULTIVATION

(71) Applicant: SUMITOMO CHEMICAL COMPANY, LIMITED, Tokyo (JP)

(72) Inventors: Norihisa Sakamoto, Kasai (JP); Mayuko Ozawa, Takarazuka (JP); Atsushi Iwata, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/944,352

(22) Filed: Jul. 17, 2013

(65) Prior Publication Data

US 2014/0020610 A1    Jan. 23, 2014

(30) Foreign Application Priority Data

Jul. 20, 2012   (JP) ................. 2012-161339

(51) Int. Cl.

| | |
|---|---|
| *A01C 7/00* | (2006.01) |
| *A01C 14/00* | (2006.01) |
| *A01C 21/00* | (2006.01) |
| *A01C 23/00* | (2006.01) |
| *A01G 1/00* | (2006.01) |
| *A01N 25/00* | (2006.01) |
| *A01N 51/00* | (2006.01) |
| *A01C 7/06* | (2006.01) |

(52) U.S. Cl.
CPC . *A01C 7/06* (2013.01); *A01C 14/00* (2013.01); *A01C 21/002* (2013.01); *A01C 23/00* (2013.01); *A01G 1/001* (2013.01); *A01N 25/00* (2013.01); *A01N 51/00* (2013.01)

(58) Field of Classification Search
CPC ......... A01N 51/00; A01N 25/00; A01G 7/00; A01G 1/001; A01C 5/00; A01C 5/04; A01C 5/06; A01C 5/062; A01C 5/066; A01C 7/00; A01C 7/08; A01C 13/00; A01C 14/00; A01C 15/00; A01C 21/00; A01C 21/002; A01C 23/00; A01C 23/006; A01C 7/06
USPC ........... 111/118, 120, 121, 129, 14, 149, 157, 111/163–170, 174, 183–188; 504/223, 349, 504/243, 100; 514/341, 357, 365, 229.2, 514/342, 471
See application file for complete search history.

(56) References Cited

U.S. PATENT DOCUMENTS

| | | |
|---|---|---|
| 4,495,875 A | 1/1985 | Makkink |
| 2005/0020640 A1 | 1/2005 | Gaulliard et al. |
| 2008/0039431 A1 | 2/2008 | Cleary et al. |
| 2008/0261810 A1 | 10/2008 | Fischer et al. |
| 2010/0317523 A1 | 12/2010 | Ikeda et al. |
| 2014/0020611 A1 | 1/2014 | Sakamoto et al. |

FOREIGN PATENT DOCUMENTS

| | | |
|---|---|---|
| JP | 2013-133308 A | 7/2013 |
| JP | 2013-133309 A | 7/2013 |
| WO | WO 02/102148 A2 | 12/2002 |
| WO | WO 2010/022917 A2 | 3/2010 |
| WO | WO 2011/134876 A1 | 11/2011 |
| WO | WO 2012/059328 A2 | 5/2012 |

OTHER PUBLICATIONS

Spanish Search Report for corresponding Spanish Application No. 201331092 dated Dec. 12, 2013 (with English translation of p. 4).
French Written Opinion and Preliminary Search Report, issued Oct. 20, 2014, for French Application No. 1357105, along with a partial English translation.
Wright et al., "Corn Insect Management," Entomological Society of America, 1999, pp. 10-21 and 44-119, ISBN: 0-938522-76-0.
A partial English translation of Hungarian Office Action for corresponding Hungarian Application No. P1300435, dated Mar. 13, 2015.
Author Unknown, "Insect Control in Field Corn," North Carolina Agricultural Chemicals Manual, Chapter 5—Insect Control, Jan. 26, 2012, pp. 65, 69-71 (http://www.nurserycropscience.info/ipm/chemical-pesticides/extension-pubs/insect-control.pdf).

*Primary Examiner* — Christopher J Novosad
(74) *Attorney, Agent, or Firm* — Birch, Stewart, Kolasch & Birch, LLP

(57) ABSTRACT

Provided is a method for reducing damage by harmful organisms in corn cultivation. Damage by harmful organisms in corn cultivation can be reduced by carrying out the steps of A) ditching a cultivated land; B) seeding with corn a furrow formed in the foregoing step; C) applying to the furrow an aqueous dispersion or aqueous solution of one or more selected from the below-mentioned compound group (I); and D) closing the furrow. Compound group (I): clothianidin, thiamethoxam, imidacloprid or thiacloprid.

17 Claims, No Drawings

METHOD FOR REDUCING DAMAGE BY HARMFUL ORGANISMS IN CORN CULTIVATION

BACKGROUND OF THE INVENTION

1. Field of the Invention

The present invention relates to a method for reducing damage by harmful organisms in corn cultivation.

2. Description of the Related Art

Previously, various methods have been known as a method for reducing damage by harmful organisms in corn cultivation.

PRIOR ART LITERATURE

Non-Patent Literature

Non-Patent Literature 1: Handbook of Corn Insects. ISBN: 0-938522-76-0, 1999. Entomological Society of America

SUMMARY OF THE INVENTION

In corn cultivation, with worldwide cereal demand expansion, various efforts have been made in order to increase a yield, but since a reduction in yield due to harmful organisms such as pests and weeds has been significant, development of a method for reducing damage by harmful organisms in corn cultivation has been desired.

The present inventors have conducted studies for finding out a method for reducing damage by harmful organisms in corn cultivation, and resultantly found out that damage by harmful organisms in corn cultivation can be reduced by carrying out the steps of: A) making a furrow in a cultivated land (hereinafter, referred to as step A in some cases); B) seeding with corn a furrow formed in the foregoing step (hereinafter, referred to as step B in some cases); C) applying to the furrow an aqueous dispersion or aqueous solution of one or more selected from the below-mentioned compound group (I) (hereinafter, referred to as the present compound (I) in some cases) (hereinafter, referred to as step C in some cases); and D) closing the furrow (hereinafter, referred to as step D in some cases).

That is, the present invention is as follows:

[1] A method for reducing damage by harmful organisms in corn cultivation, the method including the steps of:
A) making a furrow in a cultivated land; B) seeding with corn a furrow formed in the foregoing step; C) applying to the furrow an aqueous dispersion or aqueous solution of one or more selected from the below-mentioned compound group (I); and D) closing the furrow.
(compound group (I): group consisting of clothianidin, thiamethoxam, imidacloprid and thiacloprid)

[2] The method according to [1], wherein the furrow is made to a depth of 1 to 10 cm.

[3] The method according to [1] or [2], wherein making furrow is performed using a disk furrow opener.

[4] The method according to any one of [1] to [3], wherein seeding is performed using a pneumatic seeder.

[5] The method according to any one of [1] to [4], wherein one or more selected from the compound group (I) are applied in an amount of 5 to 500 g per hectare of the cultivated land which is seeded with corn.

[6] The method according to any one of [1] to [5], wherein an aqueous dispersion or aqueous solution of one or more selected from the compound group (I) is applied in an amount of 10 to 1000 liters per hectare of the cultivated land which is seeded with corn.

[7] The method according to any one of [1] to [6], wherein the type of application is spraying, dripping or drenching.

[8] The method according to any one of [1] to [6], wherein the type of application is spraying.

[9] The method according to any one of [1] to [8], wherein the harmful organism is one or more pests selected from the group consisting of *Agriotes* spp., *Diabrotica* spp., *Agrotis* spp. and *Rhopalosiphum* spp.

[10] The method according to anyone of [1] to [9], wherein the corn is hybrid variety corn.

[11] The method according to anyone of [1] to [10], wherein the corn seed is a corn seed treated with one or more fungicides selected from the group consisting of fludioxonil, metalaxyl, metalaxyl-M, thiuram, triticonazole, carboxin, prochloraz, prothioconazole, sedaxane, penflufen, fluxapyroxad, trifloxystrobin, pyraclostrobin and difenoconazole.

[12] The method to any one of [1] to [11], which further includes a step of applying one or more herbicides selected from the group consisting of mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluoroxypyr, pethoxamid, flumioxazin, thiencarbazone-methyl and iodosulfuron-methyl-sodium salt to a cultivated land, before the furrow making step or after the furrow closing step.

[13] The method according to anyone of [1] to [12], wherein a seed of corn treated with one or more safeners selected from the group consisting of isoxadifen-ethyl, furilazole, dichlormid, benoxacor and cyprosulfamide is used in the seeding step.

[14] The method according to any one of [1] to [12], wherein an aqueous dispersion or aqueous solution of one or more selected from the compound group (I) and one or more safeners selected from the group consisting of isoxadifen-ethyl, furilazole, dichlormid, benoxacor and cyprosulfamide is applied.

[15] The method according to any one of [1] to [12], which further includes a step of applying to the cultivated land one or more safeners selected from the group consisting of isoxadifen-ethyl, furilazole, dichlormid, benoxacor and cyprosulfamide before the furrow making step or after the furrow closing step.

[16] The method according to any one of [1] to [15], wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (I).

[17] The method according to any one of [1] to [16], wherein the aqueous dispersion or aqueous solution of one or more selected from the compound group (I) is an aqueous dispersion or aqueous solution of clothianidin.

[18] The method according to any one of [1] to [16], wherein the aqueous dispersion or aqueous solution of one or more selected from the compound group (I) is an aqueous dispersion or aqueous solution of imidacloprid.

According to the present invention, harmful organisms in corn cultivation can be prevented, therefore, damage by harmful organisms in corn cultivation can be reduced.

DETAILED DESCRIPTION OF THE PREFERRED EMBODIMENTS

For the order of carrying out steps, usually, a step A, and then steps B and C are carried out. In the step A, usually, a furrow having a V-shaped cross section is formed in a linear shape on a cultivated land. The step A may be carried out, followed by carrying out the step B, and then the step C, or the order may be reversed. The steps B and C may be carried out in parallel. Usually, a step D is carried out after the steps B and C.

In the present invention, usually, a seeder which is pulled with a tractor is used. Examples of the seeder include a composite-type seeder including a ditching part for forming a furrow, a seeding part for seeding a furrow in a speed linkage manner through piping from a hopper box filled with a seed, an agricultural chemical application part for applying the aqueous dispersion or aqueous solution in a speed linkage manner through piping from a reservoir filled with the aqueous dispersion and aqueous solution, a furrow closing part for closing the furrow by gathering together a soil on the side of the formed furrow, and so on.

The ditching part of a seeder is usually attached to a front part of the seeder, and a furrow is formed on a cultivated land with movement of a tractor. Examples of the ditching part include a ploughshare furrow opener and a disk furrow opener, and a ditching system using a disk furrow opener which has a strong force of cutting a crop residue, has a small reduction in a cutting force due to adhesion of a soil, and can stabilize the depth of a furrow is preferable in that a furrow can be seeded and the aqueous dispersion or aqueous solution can be applied to the furrow uniformly due to stabilization of a depth of a furrow, so that the effect of a chemical is stabilized.

The depth of the furrow formed on a cultivated land can be appropriately changed depending on the soil condition of a place of corn cultivation, the condition of cultivating corn thereafter, and the weather condition, and is usually 1 to 10 cm, preferably 2 to 8 cm, further preferably 2 to 6 cm.

The seeding part of the seeder is usually attached to a rear of the ditching part, and the furrow is seeded with movement of a tractor. Examples of the seeding part include a mechanical seeder and a pneumatic seeder, and the pneumatic seeder using air pressure is preferable in that seed clogging or seeding leakage is small, so that seeding is stably performed, and a seed can be seeded in a furrow orderly. Examples of the pneumatic seeder include a vacuum suction type seeder and a blowing type seeder, and based on the reason of imparting little damage to a seed, a vacuum suction type seeder is preferable.

In the present invention, the present compound (I) is used, and particularly clothianidin or imidacloprid is preferably used.

Clothianidin is a known compound, and is described in, for example, "The Pesticide Manual—15$^{th}$ edition (published by BCPC); ISBN 978-1-901396-18-8", page 229. This compound is obtained from a commercially available preparation, or is obtained by production using a known method.

Thiamethoxam is a known compound, and is described in, for example, "The Pesticide Manual—15$^{th}$ edition (published by BCPC); ISBN 978-1-901396-18-8", page 1112. This compound is obtained from a commercially available preparation, or is obtained by production using a known method.

Imidacloprid is a known compound, and is described in, for example, "The Pesticide Manual—15$^{th}$ edition (published by BCPC); ISBN 978-1-901396-18-8", page 645. This compound is obtained from a commercially available preparation, or is obtained by production using a known method.

Thiacloprid is a known compound, and is described in, for example, "The Pesticide Manual—15$^{th}$ edition (published by BCPC); ISBN 978-1-901396-18-8", page 1111. This compound is obtained from a commercially available preparation, or is obtained by production using a known method.

The present compound (I) for use in the present invention may be the present composition (I) itself, but is usually formulated into a dosage form which is usually diluted with water and used, by mixing the present compound (I) with an appropriate solid carrier or liquid carrier, and adding a surfactant and other formulation additives for a preparation as necessary. Examples of the dosage form which is usually diluted with water and used include a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate and a dry flowable.

Examples of the solid carrier used upon formulation into a preparation include natural or synthetic minerals such as clay, kaolin, talc, bentonite, sericite, sulfur, active carbon, calcium carbonate, diatomaceous earth, quartz, pumice stone, calcite, meerschaum, dolomite, olivine, pyroxene, amphibole, feldspar, silica, alumina, vermiculite, and perlite; and fine grains of an elastomer, a plastic, a ceramic, a metal, sawdust, corncob, a kernel shell of coconut, a stem of tobacco and the like.

Examples of the liquid carrier include water, xylene, methanol, butanol, pentanol, benzyl alcohol, cyclohexanon, gamma-butyrolactone, N-methyl-pyrrolidone, N-octyl-pyrrolidone, glycol diacetate, glycols, fatty acid dimethylamides, fatty acids and fatty acid esters. They may be mixed and used.

Examples of the surfactant include common nonionic surfactants, cationic surfactants, anionic surfactants and amphoteric surfactants, and one or more thereof are used.

Examples of the surfactant include an alkylsulfuric acid salt, an alkylsulfuric acid ester salt, an alkylsulfonic acid salt, an alkylarylsulfonic acid salt, a lignosulfonic acid ester, a naphthalenesulfonic acid salt, a phenolsulfonic acid salt, a dibutylnaphthalenesulfonic acid salt, a fatty alcohol sulfuric acid salt, fatty acid alkyl aryl ethers and polyoxyethylene compounds thereof, polyethylene glycol ethers, polyethylene glycol fatty acid esters, polyhydric alcohol esters, a sugar alcohol derivative and a silicone-based surfactant.

Examples of the other formulation additives for a preparation include an emulsifier, a dispersant, an antifoamer, a stabilizer, an antiseptic and a colorant.

Examples of the preferred emulsifier include a nonionic emulsifier and an anionic emulsifier (e.g. a polyoxyethylene fatty alcohol ether, an alkyl sulfonate and an aryl sulfonate). Examples of the dispersant include a lignin sulfurous acid waste liquid and methyl cellulose.

Examples of the preferred antifoamer include a silicone or magnesium stearate-based antifoamer.

Further, for example, glycerin, ethylene glycol and propylene glycol may be added as an antifreezing agent.

The aqueous dispersion or aqueous solution of the present compound (I) which is used in the step C in the present invention can be obtained by dispersing or dissolving the present compound (I) in water. Preferably an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains the present compound (I). The aqueous dispersion or aqueous solution may contain a herbicide, a safener and the like.

The aqueous dispersion of the present compound (I) in the present invention includes a liquid formed by suspending the present compound (I) in water in a solid state, and a liquid formed by emulsifying the present compound (I) in water in a liquid state.

The application amount of the present compound (I) in the present invention can be appropriately changed depending on the condition of cultivating corn thereafter and the weather condition, and is usually 5 to 500 g, preferably 10 to 400 g per hectare of a cultivated land which is seeded with corn.

The application amount of the aqueous dispersion or aqueous solution can be appropriately changed depending on the condition of cultivating corn thereafter and the weather condition, and is usually 10 to 1000 liters, preferably 50 to 500 liters, further preferably 50 to 300 liters per hectare of a cultivated land which is seeded with corn.

Usually, the aqueous dispersion or aqueous solution is stored in a reservoir attached to a tractor body or a seeder pulled with a tractor, and is applied, in linkage with or independently of a vehicle speed, through piping from the reservoir with movement of the tractor.

The type of application is not particularly limited as long as it is capable of application into a furrow, but particularly spraying, dripping or drenching is preferable.

When the type of application is spraying, dripping or drenching, by applying a pressure with a pump or adjusting the opening of a valve of a reservoir or a hose, the application amount can be adjusted to perform uniform application to a furrow.

The furrow closing part is usually made of rubber or made of cast iron, has a wheel shape, and closes a furrow by gathering together on the side of the furrow with movement of a tractor.

The present invention can reduce damage by harmful organisms in corn cultivation.

In the present invention, the harmful organism refers to pests, weeds and the like.

Specific examples of vermin which can be controlled by the present invention include vermin belonging to *Agriotes* spp., *Diabrotica* spp., *Agrotis* spp., *Myzus* spp., *Aphis* spp., *Ostrinia* spp., *Zyginidia* spp., *Sesamia* spp., *Oscinella* spp., *Sitobion* spp., *Scutigerella* spp., *Astylus* spp., *Rhopalosiphum* spp., *Metopolophium* spp., *Melanotus* spp. and *Melolontha* spp., and the present invention is preferably applied as a method for reducing damage by particularly *Agriotes* spp., *Diabrotica* spp., *Agrotis* spp. and *Rhopalosiphum* spp.

The variety of corn, to which the present invention can be applied, is not particularly limited, but application of corn to a hybrid variety is preferable. The hybrid variety is first cross obtained by mating two different type of varieties, and generally has more excellent characteristics than those of both parents.

Corn may be corn to which resistance has been imparted by a genetic engineering technique or a breeding method by mating.

The corn seed used in the present invention is preferably treated with a fungicide, and examples of the fungicide include fludioxonil, metalaxyl, metalaxyl-M, thiuram, triticonazole, carboxin, prochloraz, prothioconazole, sedaxane, penflufen, fluxapyroxad, trifloxystrobin, pyraclostrobin and difenoconazole, and fludioxonil, metalaxyl-M, thiuram, triticonazole, sedaxane, penflufen, and fluxapyroxad are preferable, and fludioxonil, metalaxyl-M and thiuram are more preferable. The corn seed is used after being treated with one or more of these fungicides. Alternatively, a commercially available treated seed may be purchased and used.

It is preferable to apply a herbicide to a cultivated land before the step A or after the step D in order to suppress generation of weeds during a cultivation term of corn, and examples of the herbicide include mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluoroxypyr, pethoxamid, flumioxazin, thiencarbazone-methyl, iodosulfuron-methyl-sodium salt, prosulfuron, topramezone, metosulam, cycloxydim, aclonifen, dimethenamid, florasulam, clopyralid, flazasulfuron, imazamox, MCPA, 2,4-D, linuron, propisochlor, thifensulfuron methyl and tritosulfuron; preferably mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluoroxypyr, pethoxamid, flumioxazin, thiencarbazone-methyl, iodosulfuron-methyl-sodium salt, prosulfuron, topramezone, metosulam, cycloxydim and aclonifen; more preferably mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluoroxypyr, pethoxamid, flumioxazin, thiencarbazone-methyl and iodosulfuron-methyl-sodium salt. Usually, one or more of these herbicides are applied. When two or more thereof are applied, they may be applied simultaneously, or they may be applied separately. When they are applied separately, they may be applied on the same day, or on another day.

In the present invention, a safener can also be applied in combination with a herbicide. Examples of the safener include isoxadifen-ethyl, furilazole, dichlormid, benoxacor and cyprosulfamide. The method for applying the safener is not particularly limited, and can be applied together with the present compound (I) in the step C, and at this time, a preparation containing the present compound (I) and the safener may be used alone, or a preparation containing the present compound (I) and a preparation containing the safener may be used in combination. Alternatively, the safener can be applied before the step A or after the step D. A corn seed treated with the safener can be used. A corn seed may be treated with one or more of the aforementioned safeners and then used, or a commercially available treated seed may be purchased and used.

EXAMPLES

Next the present invention will be further described by way of the following examples, but the present invention is not limited to these examples.

Example 1

Using a pneumatic seeder (disk furrow opener, manufactured by Gaspardo) equipped with a power sprayer (trade name: WJR 2525, manufactured by HONDA), a cultivated land was ditched at intervals of 75 cm to a depth of 3 cm from the soil surface, and the furrow was seeded with corn (*Zea Mays*, trade name: DK 440; hybrid variety, manufactured by Monsanto) at intervals of 13 cm. A seeding density of corn was 100000 seeds/ha. Then, the furrow was spray-treated with an aqueous suspension of a clothianidin water dispersible granule (using a 50% dispersible granule, trade name: Dantop 50WG, manufactured by Philagro) at 100 L/ha so that the application amount of clothianidin was 50 g/ha, and then a soil on the side of the furrow was gathered together to close the furrow. This was defined as an example section 1.

For comparison, a non-treatment section, which was seeded with corn without application of a clothianidin water dispersible granule, was provided.

In any section, four places were arranged by a randomized block method, with one place having an area of 15 m² (5 m×3 m).

For suppressing generation of weeds, the whole cultivated land was spray-treated with a herbicide, a mixed agent of S-metolachlor, atrazine and mesotrione (using 537.5 g/L of an EC preparation, trade name: Lumax, manufactured by Syngenta) at 3.5 L/ha in terms of an application amount of the preparation on the same day as the treatment with the clothianidin water dispersible granule.

35 days after application of the clothianidin water dispersible granule, the number of plants of corn damaged by *Agriotes* spp. in each of the example section 1 and the non-treatment section was investigated, a damage plant rate was calculated in accordance with the following equation, and then an average damage plants rate of the four investigation sections was determined.

Damage plant rate(%)=[(number of plants of corn damaged)/(number of plants of corn seeded)]×100

The results are shown in Table 1.

TABLE 1

|  | Application amount of clothianidin (g/ha) | Damage plant rate (%) |
|---|---|---|
| Example section 1 | 50 | 0 |
| Non-treatment section | 0 | 43 |

Example 2

Using a pneumatic seeder (disk furrow opener, manufactured by Gaspardo) equipped with a power sprayer (trade name: WJR 2525, manufactured by HONDA), a cultivated land was ditched at intervals of 75 cm to a depth of 3 cm from the soil surface, and the furrow was seeded with corn (*Zea Mays*, trade name: DK 440; hybrid variety, manufactured by Monsanto) at intervals of 12 cm. A seeding density of corn was 100000 seeds/ha. Then, the furrow was spray-treated with an aqueous suspension of a clothianidin water dispersible granule (using a 50% dispersible granule, trade name: Dantop 50WG, manufactured by Philagro) at 100 L/ha so that the application amount of clothianidin was 50 g/ha, and then a soil on the side of the furrow was gathered together to close the furrow. This was defined as an example section 2.

For comparison, a non-treatment section, which was seeded with corn without application of a clothianidin water dispersible granule, was provided.

In any section, four places were arranged by a randomized block method, with one place having an area of 15 m² (5 m×3 m).

34 days after application of the clothianidin water dispersible granule, the number of plants of corn damaged by *Agriotes* spp. in each of the example section 2 and the non-treatment section was investigated, a damage plant rate was calculated in accordance with the following equation, and then an average damage plants rate of the four investigation sections was determined.

Damage plant rate(%)=[(number of plants of corn damaged)/(number of plants of corn seeded)]×100

The results are shown in Table 2.

TABLE 2

|  | Application amount of clothianidin (g/ha) | Damage plant rate (%) |
|---|---|---|
| Example section 2 | 50 | 7.7 |
| Non-treatment section | 0 | 73.3 |

Example 3

A cultivated land was ditched at intervals of 75 cm to a depth of 3 cm from the soil surface, and the furrow was seeded with corn (*Zea Mays*, variety name: KUBRIK; hybrid variety) at intervals of 17 cm. A seeding density of corn was 78000 seeds/ha. Then, the furrow was spray-treated with an aqueous suspension of a clothianidin water dispersible granule (using a 50% water dispersible granule, trade name: Dantop 50WG, manufactured by Philagro) at 100 L/ha so that the application amount of clothianidin was 25 g/ha, and then a soil on the side of the furrow was gathered together to close the furrow. This was defined as an example section 3.

For comparison, a non-treatment section, which was seeded with corn without application of a clothianidin water dispersible granule, was provided.

In any section, four places were arranged by a randomized block method, with one place having an area of 54 m² (18 m×3 m).

34 days after application of the clothianidin water dispersible granule, the number of plants of corn damaged by *Agriotes sordidus* in each of the example section 3 and the non-treatment section was investigated, a damage plant rate was calculated in accordance with the following equation, and then an average damage plants rate of the four investigation sections was determined.

Damage plant rate(%)=[(number of plants of corn damaged)/(number of plants of corn seeded)]×100

The results are shown in Table 3.

TABLE 3

|  | Application amount of clothianidin (g/ha) | Damage plant rate (%) |
|---|---|---|
| Example section 3 | 25 | 1.8 |
| Non-treatment section | 0 | 34.6 |

Example 4

Ammonium phosphate (N:P:K=12:52:0) and urea (N:P:K=46:0:0), each of which being a fertilizer, were applied to the soil surface of a cultivated land at 100 kg/ha and 260 kg/ha, respectively, and the cultivated land was plowed.

24 days after fertilization, using a pneumatic seeder (disk furrow opener) equipped with a power sprayer, a cultivated land was ditched at intervals of 75 cm to a depth of 5 cm from the soil surface, and the furrow was seeded with corn (*Zea Mays*, variety name: DKC 5143; hybrid variety, manufactured by Monsanto). The cultivated land was seeded at intervals of 20 cm using, as a corn seed, one treated with a mixed agent of metalaxyl-M and fludioxonil (trade name: Maxim XL, manufactured by Syngenta). A seeding density of corn was 66667 seeds/ha. Then, the furrow was spray-treated with an aqueous suspension of a clothianidin water dispersible granule (using a 50% water dispersible granule, trade name: Dantop 50WG, manufactured by Philagro Company) at 125 L/ha so that the application amount of clothianidin was 80 g/ha, and then a soil on the side of the furrow was gathered together to close the furrow. This was defined as an example section 4.

For comparison, a non-treatment section, which was seeded with corn without application of a clothianidin water dispersible granule, was provided.

In any section, four places were arranged by a randomized block method, with one place having an area of 45 m$^2$ (15 m×3 m).

17 days after application of the clothianidin water dispersible granule, the number of plants of corn germinated was investigated, with central two rows of four rows of seeded furrows as an investigation section, for the example section 4 and the non-treatment section. On the same day, in order to suppress generation of weeds, the whole cultivated land was spray-treated with a nicosulfuron wettable powder (using 40 g/L SC preparation, trade name: Milagro, manufactured by Syngenta) and a mesotrione wettable powder (using 100 g/L SC preparation, trade name: Callisto, manufactured by Syngenta), each of which being a herbicide, at 0.75 L/ha and 0.25 L/ha, respectively, in terms of an application amount of the preparation.

165 days after application of the clothianidin water dispersible granule, the number of plants of corn lodged due to damage by *Diabrotica virgifera virgifera* and *Agriotes lineatus* in the furrows of the example section 4 and the non-treatment section, for which the number of plants of corn germinated was investigated, was investigated, a lodge rate was calculated in accordance with the following equation, and then an average lodge rate for the four investigation sections was determined.

Lodge rate(%)=[(number of plants of corn lodged)/ (number of plants of corn germinated)]×100

The results are shown in Table 4.

TABLE 4

| | Application amount of clothianidin (g/ha) | Lodge rate (%) |
|---|---|---|
| Example section 4 | 80 | 4 |
| Non-treatment section | 0 | 23 |

Example 5

A chemical fertilizer (N:P:K=15:15:15) was applied to the soil surface of a cultivated land at 300 kg/ha, and the cultivated land was then plowed.

In order to prevent generation of weeds, 28 days after fertilization, the whole cultivated land was spraying-treated with a mixed agent (using 610 g/kg water dispersible granule, trade name: MaisTer, manufactured by Bayer CropScience) of foramsulfuron and an iodosulfuron-methyl-sodium salt, each of which being a herbicide, and a safener, isoxadifen-ethyl, at 0.15 L/ha in terms of an application amount of the preparation.

3 days after application of the preparation, using a pneumatic seeder (disk furrow opener) equipped with a power sprayer, a cultivated land was ditched at intervals of 75 cm to a depth of 5 cm from the soil surface, and the furrow was seeded with corn (variety name: DKC 5143; hybrid variety, manufactured by Monsanto). The cultivated land was seeded at intervals of 20 cm using, as a corn seed, one treated with a mixed agent of metalaxyl-M and fludioxonil (trade name: Maxim XL, manufactured by Syngenta). A seeding density of corn was 66667 seeds/ha. Then, the furrow was spray-treated with an aqueous suspension of a clothianidin water dispersible granule (using a 50% water dispersible granule, trade name: Dantop 50WG, manufactured by Philagro Company) at 125 L/ha so that the application amount of clothianidin was 80 g/ha, and then a soil on the side of the furrow was gathered together to close the furrow. This was defined as an example section 5.

For comparison, a non-treatment section, which was seeded with corn without application of a clothianidin water dispersible granule, was provided.

In any section, four places were arranged by a randomized block method, with one place having an area of 45 m$^2$ (15 m×3 m).

18 days after application of the clothianidin water dispersible granule, the number of plants of corn germinated was investigated, with central two rows of four rows of seeded furrows as an investigation section, for the example section 5 and the non-treatment section.

155 days after application of the clothianidin water dispersible granule, the number of plants of corn lodged due to damage by *Diabrotica virgifera virgifera* and *Agriotes lineatus* in the furrows of the example section 5 and the non-treatment section, for which the number of plants of corn germinated was investigated, was investigated, a lodge rate was calculated in accordance with the following equation, and then an average lodge rate for the four investigation sections was determined.

Lodge rate [%]=[(number of plants of corn lodged)/ (number of plants of corn germinated)]×100

The results are shown in Table 5.

TABLE 5

| | Application amount of clothianidin (g/ha) | Lodge rate (%) |
|---|---|---|
| Example section 5 | 80 | 0 |
| Non-treatment section | 0 | 36 |

Example 6

A plastic cup (diameter 7 cm) having a volume of 390 ml was filled with a soil, a furrow was formed to a depth of 3 cm from the soil surface, the formed furrow was drip-treated with each of water-diluted liquids of a thiamethoxam water soluble powder (using a 10.0% preparation, trade name: Actara Water Soluble Powder, manufactured by Syngenta Japan K.K.), an imidacloprid water dispersible granule (using a 50.0% preparation, trade name: Admire Water dispersible Granule, manufactured by Bayer CropScience K.K.) and a thiacloprid water dispersible granule (using a 30.0% preparation, trade name: Bariard Water Dispersible Granule, manufactured by Bayer CropScience K.K.) so as to achieve the application amount described in Table 6, and then seeded with corn (variety name: Pioneer 32K61, hybrid variety) at a rate of one grain per cup, and the soil on the side of the furrow was gathered together to close the furrow. Corn was grown in a usual green house.

10 days after seeding of corn, 10 insects of *Rhopalosiphum padi* were released in each cup. This is called a treatment section.

On the other hand, except that a chemical was not applied, corn was grown in a usual green house in the same manner as in the treatment section, and 10 insects of *Rhopalosiphum padi* were released. This is called a non-chemical-treatment section.

7 days after insect releasing, the number of *Rhopalosiphum padi* was investigated, and a preventive value was calculated using the following equation. The results are shown in Table 6.

preventive value=100×(A−B)/A

A: number of insects during investigation of non-chemical-treatment section

B: number of insects during investigation of treatment section

TABLE 6

| | Application amount | Preventive value |
|---|---|---|
| Example section 6 | Thiamethoxam 20 g/ha | 100 |
| Example section 7 | Thiamethoxam 200 g/ha | 100 |
| Example section 8 | Imidacloprid 20 g/ha | 100 |
| Example section 9 | Imidacloprid 200 g/ha | 100 |
| Example section 10 | Thiacloprid 20 g/ha | 100 |
| Example section 11 | Thiacloprid 200 g/ha | 100 |

Example 7

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, and cyprosulfamide which is a safener at 150 L/ha so that the application amounts of thiencarbazone-methyl, isoxaflutole and cyprosulfamide are 9.2 g/ha, 23 g/ha and 15 g/ha, respectively.

21 days after fertilization, using a pneumatic seeder (disk furrow opener) equipped with a power sprayer, a cultivated land is ditched at intervals of 75 cm to a depth of 5 cm from the soil surface, and the furrow is seeded with corn (*Zea Mays*; hybrid variety). The furrow is seeded at intervals of 20 cm using, as a seed of corn, one treated with thiuram. A seeding density of corn is 70000 seeds/ha. In parallel with seeding of corn, an aqueous suspension of clothianidin is applied to the furrow such that the chemical is in direct contact with the seed. The furrow is spray-treated at 125 L/ha so that the application amount of clothianidin is 50 g/ha, and then a soil on the side of the furrow is gathered together to close the furrow. This is called a treatment section.

For comparison, the furrow is seeded with corn by the operation same as that in the treatment section except that an aqueous suspension of clothianidin is not applied. This is called a non-treatment section.

In any section, four places are arranged by a randomized block method, with one place having an area of 45 m$^2$ (15 m×3 m).

17 days after application of the aqueous suspension of clothianidin, the number of plants of corn germinated is investigated, with central two rows of four rows of seeded furrows as an investigation section, for the treatment section and the non-treatment section. 165 days after application of the aqueous suspension of clothianidin, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate(%)=[(number of plants of corn lodged)/(number of plants of corn germinated)]×100

As a result, the treatment section shows a low lodge rate as compared to the non-treatment section, and is found to have reduced damage by harmful organisms in corn cultivation.

Example 8

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, and cyprosulfamide which is a safener at 150 L/ha so that the application amounts of thiencarbazone-methyl, isoxaflutole and cyprosulfamide are 9.2 g/ha, 23 g/ha and 15 g/ha, respectively.

21 days after fertilization, using a pneumatic seeder (disk furrow opener) equipped with a power sprayer, a cultivated land is ditched at intervals of 75 cm to a depth of 3 cm from the soil surface, and the furrow is seeded with corn (*Zea Mays*; hybrid variety). The furrow is seeded at intervals of 20 cm using, as a seed of corn, one treated with thiuram. A seeding density of corn is 70000 seeds/ha. In parallel with seeding of corn, an aqueous suspension of imidacloprid is applied to the furrow such that the chemical is in direct contact with the seed. The furrow is spray-treated at 125 L/ha so that the application amount of imidacloprid is 120 g/ha, and then a soil on the side of the furrow is gathered together to close the furrow. This is called a treatment section.

For comparison, the furrow is seeded with corn by the operation same as that in the treatment section except that an aqueous suspension of imidacloprid is not applied. This is called a non-treatment section.

In any section, four places are arranged by a randomized block method, with one place having an area of 45 m$^2$ (15 m×3 m).

17 days after application of the aqueous suspension of imidacloprid, the number of plants of corn germinated is investigated, with central two rows of four rows of seeded furrows as an investigation section, for the treatment section and the non-treatment section. 165 days after application of the aqueous suspension of imidacloprid, the number of plants of corn lodged due to damage by *Diabrotica virgifera vir-*

*gifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate(%)=[(number of plants of corn lodged)/ (number of plants of corn germinated)]×100

As a result, the treatment section shows a low lodge rate as compared to the non-treatment section, and is found to have reduced damage by harmful organisms in corn cultivation.

Example 9

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, at 150 L/ha so that the application amounts of thiencarbazone-methyl and isoxaflutole are 9.2 g/ha and 23 g/ha.

21 days after fertilization, using a pneumatic seeder (disk furrow opener) equipped with a power sprayer, a cultivated land is ditched at intervals of 75 cm to a depth of 5 cm from the soil surface, and the furrow is seeded with corn (*Zea Mays*; hybrid variety). The furrow is seeded at intervals of 20 cm using, as a seed of corn, one treated with thiuram and cyprosulfamide. A seeding density of corn is 70000 seeds/ha. In parallel with seeding of corn, an aqueous suspension of clothianidin is applied to the furrow such that the chemical is in direct contact with the seed. The furrow is spray-treated at 125 L/ha so that the application amount of clothianidin is 50 g/ha, and then a soil on the side of the furrow is gathered together to close the furrow. This is called a treatment section.

For comparison, the furrow is seeded with corn by the operation same as that in the treatment section except that an aqueous suspension of clothianidin is not applied. This is called a non-treatment section.

In any section, four places are arranged by a randomized block method, with one place having an area of 45 m$^2$ (15 m×3 m).

17 days after application of the aqueous suspension of clothianidin, the number of plants of corn germinated is investigated, with central two rows of four rows of seeded furrows as an investigation section, for the treatment section and the non-treatment section. 165 days after application of the aqueous suspension of clothianidin, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate(%)=[(number of plants of corn lodged)/ (number of plants of corn germinated)]×100

As a result, the treatment section shows a low lodge rate as compared to the non-treatment section, and is found to have reduced damage by harmful organisms in corn cultivation.

Example 10

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, at 150 L/ha so that the application amounts of thiencarbazone-methyl and isoxaflutole are 9.2 g/ha and 23 g/ha, respectively.

21 days after fertilization, using a pneumatic seeder (disk furrow opener) equipped with a power sprayer, a cultivated land is ditched at intervals of 75 cm to a depth of 3 cm from the soil surface, and the furrow is seeded with corn (*Zea Mays*; hybrid variety). The furrow is seeded at intervals of 20 cm using, as a seed of corn, one treated with thiuram. A seeding density of corn is 70000 seeds/ha. In parallel with seeding of corn, an aqueous suspension of imidacloprid and cyprosulfamide which is a safener is applied to the furrow such that the chemical is in direct contact with the seed. The furrow is spray-treated at 125 L/ha so that the application amounts of imidacloprid and cyprosulfamide are 120 g/ha and 15 g/ha, and then a soil on the side of the furrow is gathered together to close the furrow. This is called a treatment section.

For comparison, the furrow is seeded with corn by the operation same as that in the treatment section except that an aqueous suspension of imidacloprid and cyprosulfamide is not applied. This is called a non-treatment section.

In any section, four places are arranged by a randomized block method, with one place having an area of 45 m$^2$ (15 m×3 m).

17 days after application of the aqueous suspension of imidacloprid, the number of plants of corn germinated is investigated, with central two rows of four rows of seeded furrows as an investigation section, for the treatment section and the non-treatment section. 165 days after application of the aqueous suspension of imidacloprid, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate(%)=[(number of plants of corn lodged)/ (number of plants of corn germinated)]×100

As a result, the treatment section shows a low lodge rate as compared to the non-treatment section, and is found to have reduced damage by harmful organisms in corn cultivation.

What is claimed is:

1. A method for reducing damage by harmful organisms in corn cultivation, the method comprising the steps of:
    A) making a furrow in a cultivated land; B) seeding with corn a furrow formed in the foregoing step; C) applying to the furrow an aqueous dispersion or aqueous solution of one or more selected from the below-mentioned compound group (I); and D) closing the furrow, wherein the furrow is made ditched to a depth of 2 to 8 cm,
    compound group (I): clothianidin, thiamethoxam, imidacloprid or thiacloprid.

2. The method according to claim 1, wherein making furrow is performed using a disk furrow opener.

3. The method according to claim 1, wherein seeding is performed using a pneumatic seeder.

4. The method according to claim 1, wherein one or more selected from the compound group (I) are applied in an amount of 5 to 500 g per hectare of the cultivated land which is seeded with corn.

5. The method according to claim 1, wherein an aqueous dispersion or aqueous solution of one or more selected from the compound group (I) is applied in an amount of 10 to 1000 liters per hectare of the cultivated land which is seeded with corn.

6. The method according to claim 1, wherein the type of application is spraying, dripping or drenching.

7. The method according to claim 1, wherein the type of application is spraying.

8. The method according to claim 1, wherein the harmful organism is one or more pests selected from the group consisting of *Agriotes* spp., *Diabrotica* spp., *Agrotis* spp. and *Rhopalosiphum* spp.

9. The method according to claim 1, wherein the corn is hybrid variety corn.

10. The method according to claim 1, wherein the corn seed is a corn seed treated with one or more fungicides selected from the group consisting of fludioxonil, metalaxyl, metalaxyl-M, thiuram, triticonazole, carboxin, prochloraz, prothioconazole, sedaxane, penflufen, fluxapyroxad, trifloxystrobin, pyraclostrobin and difenoconazole.

11. The method according to claim 1, which further comprises a step of applying one or more herbicides selected from the group consisting of mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluroxypyr, pethoxamid, flumioxazin, thiencarbazone-methyl and iodosulfuron-methyl-sodium salt to a cultivated land, before the furrow making step or after the furrow closing step.

12. The method according to claim 1, wherein a seed of corn treated with one or more safeners selected from the group consisting of isoxadifen-ethyl, furilazole, dichlormid, benoxacor and cyprosulfamide is used in the seeding step.

13. The method according to claim 1, wherein an aqueous dispersion or aqueous solution of one or more selected from the compound group (I) and one or more safeners selected from the group consisting of isoxadifen-ethyl, furilazole, dichlormid, benoxacor and cyprosulfamide is applied.

14. The method according to claim 1, which further comprises a step of applying to the cultivated land one or more safeners selected from the group consisting of isoxadifen-ethyl, furilazole, dichlormid, benoxacor and cyprosulfamide before the furrow making step or after the furrow closing step.

15. The method according to claim 1, wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (I).

16. The method according to claim 1, wherein one or more compounds selected from the compound group (I) are clothianidin.

17. The method according to claim 1, wherein one or more compounds selected from the compound group (I) are imidacloprid.

* * * * *